(12) United States Patent
Landgraf (10) Patent No.: US 7,884,320 B2
(45) Date of Patent: Feb. 8, 2011

(54) ION MOBILITY SPECTROMETER WITH SUBSTANCE COLLECTOR

(75) Inventor: Jürgen Landgraf, Gutenberg (DE)

(73) Assignee: Brucker Daltonik GmbH, Bremen (DE)

( * ) Notice: Subject to any disclaimer, the term of this patent is extended or adjusted under 35 U.S.C. 154(b) by 236 days.

(21) Appl. No.: 12/266,402

(22) Filed: Nov. 6, 2008

(65) Prior Publication Data

US 2009/0114812 A1 May 7, 2009

(30) Foreign Application Priority Data

Nov. 6, 2007 (DE) .................. 10 2007 052 801

(51) Int. Cl.
*H01J 49/00* (2006.01)
*B01D 59/44* (2006.01)
(52) U.S. Cl. .................. 250/288; 250/283; 250/284; 250/269.1; 422/50; 422/83
(58) Field of Classification Search ......... 250/281–284, 250/288, 269.1, 435, 438, 428; 422/50, 83, 422/98
See application file for complete search history.

(56) References Cited

U.S. PATENT DOCUMENTS

| | | | |
|---|---|---|---|
| 3,621,240 A * | 11/1971 | Cohen et al. ............. 250/282 |
| 3,699,333 A | 10/1972 | Cohen et al. |
| 4,311,559 A | 1/1982 | Knowles |
| 4,311,669 A | 1/1982 | Spangler |
| 4,777,363 A | 10/1988 | Eiceman et al. |
| 5,083,019 A | 1/1992 | Spangler |
| 5,109,691 A | 5/1992 | Corrigan et al. |
| 5,420,424 A | 5/1995 | Carnahan et al. |
| 5,683,741 A * | 11/1997 | Seng et al. ............... 427/8 |
| 5,684,300 A * | 11/1997 | Taylor et al. ............. 250/286 |
| 5,723,861 A | 3/1998 | Carnahan et al. |
| 5,736,739 A | 4/1998 | Uber et al. |
| 5,763,876 A | 6/1998 | Pertinarides et al. |
| 5,811,059 A | 9/1998 | Genovese et al. |
| 5,968,837 A * | 10/1999 | Doring et al. ............. 436/173 |
| 6,803,567 B2 | 10/2004 | Leonhardt et al. |
| 7,211,791 B2 | 5/2007 | Miller et |
| 7,511,268 B2 * | 3/2009 | Landgraf ................. 250/288 |
| 7,547,880 B2 * | 6/2009 | Landgraf et al. ........... 250/287 |
| 7,579,589 B2 * | 8/2009 | Miller et al. ............... 250/292 |

(Continued)

FOREIGN PATENT DOCUMENTS

DE 195 02 674 9/1996

(Continued)

OTHER PUBLICATIONS

GB Search Report.

*Primary Examiner*—Bernard E Souw
(74) *Attorney, Agent, or Firm*—O'Shea Getz P.C.

(57) ABSTRACT

A method for operating an ion mobility spectrometer that comprises a measuring tube, a substance collector and a membrane inlet, the measuring tube, the substance collector and the membrane inlet defining a closed internal gas circuit, comprising separating the closed internal gas circuit from an external sample gas flow through the membrane inlet, transferring circulating gas containing an analyte substance from the membrane inlet to the substance collector, the analyte substance accumulated in the substance collector, releasing the accumulated analyte substances, and transferring the released analyte substances to the measuring tube.

19 Claims, 5 Drawing Sheets

U.S. PATENT DOCUMENTS

| | | |
|---|---|---|
| 2002/0016004 A1 | 2/2002 | Nguyen et al. |
| 2003/0036272 A1 | 2/2003 | Shamouilian et al. |
| 2005/0085740 A1 | 4/2005 | Davis et al. |
| 2005/0139762 A1 | 6/2005 | Miller et al. |
| 2006/0102844 A1 | 5/2006 | Sauer et al. |
| 2006/0192103 A1* | 8/2006 | Landgraf .................... 250/287 |
| 2006/0249673 A1 | 11/2006 | Breach et al. |
| 2009/0114811 A1* | 5/2009 | Landgraf .................... 250/282 |

FOREIGN PATENT DOCUMENTS

| | | |
|---|---|---|
| DE | 19938392 | 2/2001 |
| DE | 10254960 | 6/2004 |
| DE | 10310394 | 9/2004 |
| EP | 0774663 | 5/1997 |
| GB | 2052750 | 1/1981 |
| WO | 9306476 | 4/1993 |
| WO | 9738302 | 10/1997 |
| WO | 2007038302 | 4/2007 |

* cited by examiner

ION MOBILITY SPECTROMETER WITH SUBSTANCE COLLECTOR

PRIORITY INFORMATION

This patent application claims priority from German patent application 10 2007 052 801.0 filed Nov. 6, 2007, which is hereby incorporated by reference.

FIELD OF THE INVENTION

The disclosure relates generally to an ion mobility spectrometer, and in particular to an ion mobility spectrometer with a closed internal gas circuit.

BACKGROUND OF THE INVENTION

Gaseous substances are analyzed and continuously monitored in a large number of applications, such as environmental analysis, control of chemical processes, monitoring of production facilities, and in both civil and military fields for the detection of chemical warfare agents (CWAs) or explosives. Ion mobility spectrometry is a method introduced in the 1970s for high-sensitivity detection of potentially dangerous analyte substances in ambient air or other sample gases.

An ion mobility spectrometer (IMS) can be operated at ambient pressure. Ion mobility spectrometers are relatively compact and can be manufactured simply and inexpensively, making them particularly suitable for portable and mobile gas monitoring and warning devices.

Analyte substances to be detected are ionized in a reaction chamber of an ion mobility spectrometer. The ions move in a drift gas under the influence of an electrical field and are separated according to their different drift velocities, as a function of their mobility. Alternatively, in FAIMS, the dependency of their mobility on the field strength is used. If the parameters of the drift gas, such as its temperature, humidity and pressure, are held constant, then the mobility parameters of the ions are characteristic of the various substances. In the majority of mobile ion mobility spectrometers, the drift gas is circulated in a closed internal gas circuit by a pumping device, such as a gas pump or a fan. A filter incorporated into the internal gas circuit removes moisture from the circulating gas and purifies it of the analyte substances before returning the gas to the measuring tube of the ion mobility spectrometer. The parameters of the circulating gas are maintained as constant as possible inside the closed internal gas circuit. U.S. Pat. No. 4,311,669 to Spangler et al. discloses a method where the analyte substances generally enter the closed internal gas circuit of the ion mobility spectrometer through a permeable inlet membrane, on which sample gas impinges from the outside. Typically the membrane is made of silicone rubber. The majority of analyte substances permeate through the membrane relatively easier than water, thereby reducing the unfavorable ingress of moisture.

U.S. Pat. No. 5,083,019 to Spangler describes a method for increasing the detection power of an ion mobility spectrometer, by coupling the ion mobility spectrometer to a substance collector or preconcentrator. A collecting tube or a surface made of a material that adsorbs or dissolves the analyte substances to be detected, is exposed to a sample gas during a collecting phase. The analyte substances are largely accumulated in the substance collector. In a subsequent desorption phase, the collected analyte substances are released, usually by heating the substance collector. If the volume of gas that flows through the substance collector during the desorption phase is significantly lower than in the collecting phase, the concentration increases correspondingly. As a result, the detection power of the ion mobility spectrometer is increased. However, storage and delays slow penetration effects during the passage through the membrane inlet, resulting in the broadening of short analyte substance pulses released at the substance collector over time. The maximum concentration in the interior of the measuring tube is inversely proportional to the temporal broadening of the analyte substance pulse. The inverse relationship lowers the enrichment factor, in particular for slowly penetrating analyte substances of low volatility, which are particularly difficult to detect in practice. To obtain a high detection power, a correspondingly large quantity of analyte substance must be collected, which in practice causes long collection times and therefore long delay times for warnings, or high suction flows and large substance collectors, which are expensive and consume relatively large amounts of energy.

Beside a high detection power, a short warning time is an essential feature of an ion mobility spectrometer. However, disadvantageously in the aforementioned prior art, the warning time varies between a few seconds and a few minutes.

In other prior art examples, German Publications DE 199 38 392 to Leonhardt et al. and DE 10 2005 004 325 to Landgraf disclose methods in which substances are collected in substance collectors outside the internal gas circuit. The substance collectors are subsequently incorporated into the internal closed gas circuit by valves changing the gas flow circuitry.

SUMMARY OF THE INVENTION

A method for operating an ion mobility spectrometer that comprises a measuring tube, a substance collector and a membrane inlet, the measuring tube, the substance collector and the membrane inlet defining a closed internal gas circuit, comprises separating the closed internal gas circuit from an external sample gas flow through the membrane inlet, transferring circulating gas containing an analyte substance from the membrane inlet to the substance collector, the analyte substance accumulated in the substance collector, releasing the accumulated analyte substances, and transferring the released analyte substances to the measuring tube.

During a collecting phase, circulating gas, for example containing the analyte substances to be measured, is transferred from the membrane inlet into the substance collector, before passing through a pumping device and a filter, so that the analyte substances are accumulated in the substance collector. During the desorption and injection phases, the stored substances are released and transferred into the measuring tube of the ion mobility spectrometer, where they are analyzed. The analyte substances collected by the substance collector are enriched by releasing them as short substance pulses. The substance collector may be shock heated to achieve the fastest possible release (i.e., desorption) of the substances in order to generate highly concentrated, short-duration analyte substance pulses. Actively cooling the substance collector during the collecting phase may improve the storage of analyte substances in the substance collector.

A high enrichment factor may be achieved by locating the substance collector within the internal gas circuit, avoiding any temporal broadening of the released analyte substance pulse, as occurs on passage through a membrane. The internal substance collector may be located in close proximity to the measuring tube of the ion mobility spectrometer. As a result, the detection power of an ion mobility spectrometer is significantly increased. Moreover, an internal substance collector may be more compact than an external substance collector.

Locating the substance collector within the internal gas circuit protects it from dust, whereas an external collector, when exposed to heavy dust, can quickly become blocked and require replacement.

In some examples, no additional pumping devices are required to enrich the substances in an internal substance collector.

In contrast to substance collectors that collect analyte substances outside the gas circuit and then are themselves incorporated into the internal gas circuit, in some examples, only analyte substances that can penetrate through the inlet membrane are collected. This has the advantage that the ingress of water vapor and substances of very low volatility into the collector is largely prevented. An increased concentration of water vapor may lower the sensitivity of the ion mobility spectrometer. Analyte substances of relatively low volatility may be released again at relatively high temperatures. Separating them out permits lower desorption temperatures and times, thus, for example, significantly saving energy (essential for mobile instruments) and reducing the aging of the collecting material.

Releasing the analyte substances from an internal substance collector has no effect on the membrane inlet. After switching back from the desorption/injection phase to the collecting phase, it may not be necessary to wait for the permeation dead times, during which the sample gas generally cannot be monitored. Analyte substances continue to permeate from the sample gas through the membrane during the desorption/injection phase as well. Therefore an ion mobility spectrometer according to the disclosure may be operable to detect freshly arriving analyte substances in the sample gas during the desorption/injection phase.

The substance collector may be located at various points in the gas circuit. On the one hand, it may be positioned upstream of the measuring tube of the ion mobility spectrometer, so that a portion of the circulating gas that contains analyte substances passes from the membrane inlet, for example, directly into the substance collector without first reaching the measuring tube. Alternatively, the substance collector may be located downstream of the measuring tube. In this case, the circulating gas that contains analyte substances is introduced into the measuring tube, where it is partially ionized. The analyte substance that is not ionized passes the measuring tube and enters the substance collector. In this example, the direction of gas flow in the substance collector is reversed in the desorption phase. To reverse the flow, control elements, for example valves or adjustable flow resistances, are located within the internal gas circuit. The control elements are first set so that circulating gas containing analyte substances flows from the measuring tube into the substance collector. The control elements are then set so that circulating gas flows through the substance collector into the measuring tube. No matter which of the two locations in the gas circuit the substance collector is placed, it may be necessary for the circulating gas that contains analyte substances to flow through the substance collector or the measuring tube prior to reaching a filter in the gas circuit because the analyte substances are removed from the circulating gas by the filter and are therefore no longer available for analysis.

These and other objects, features and advantages of the present disclosure will become more apparent in light of the following detailed description of preferred embodiments thereof, as illustrated in the accompanying drawings.

DETAILED DESCRIPTION

Figure 1:
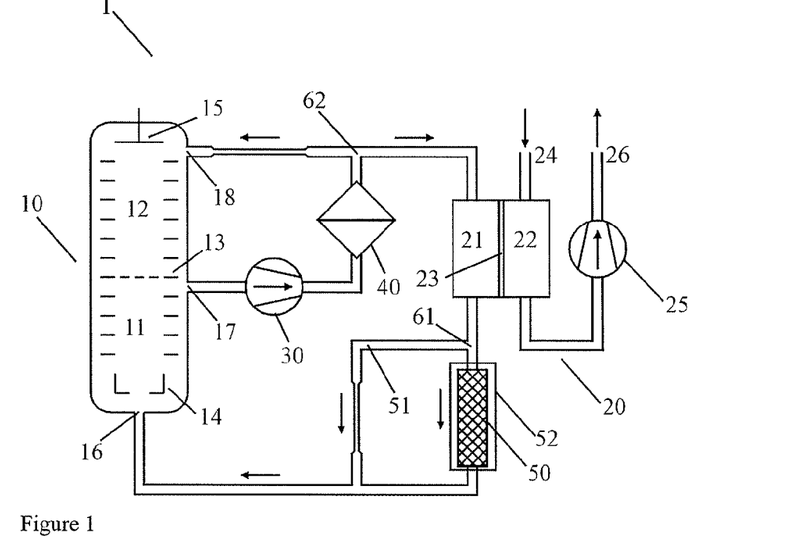
FIG. 1 illustrates a first example of an ion mobility spectrometer.

FIG. 1 illustrates a first example of an ion mobility spectrometer 1. The ion mobility spectrometer comprises an internal substance collector 50 and a measuring tube 10, for example a drift time measuring tube. Drift time ion mobility spectrometers are the most widely used ion mobility spectrometers. Therefore, this disclosure primarily contemplates the drift time ion mobility spectrometers. However, other types of ion mobility spectrometers, for example the "Aspiration Ion Mobility Spectrometer" from the Finnish company Environics Oy and the "Asymmetric Field Ion Mobility Spectrometer" (FAIMS), should not be regarded as excluded from the following disclosure.

The measuring tube 10, includes a grating grid 13 that separates a reaction chamber 11 and a drift chamber 12. Generally, gas molecules are ionized in the reaction chamber 11 and relatively close to a radiation source 14. In one example, the radiation source 14 comprises a beta emitter such as $^{63}$Nickel. Analyte substances enter the reaction chamber 11 with circulating gas and are, for example, ionized by a cascade of reactions with the gas molecules (e.g., nitrogen and water), ending with complex ions which are able to ionize the analyte molecules by protonation. The created analyte ions drift in the reaction chamber 11 under the influence of an electric field towards the gating grid 13. The electric gating grid 13 may be briefly opened to admit pulses of ions into the drift chamber 12, where the ions drift in an axial electrical field toward a detector electrode 15. The substance-specific drift velocities separate ions with different ion mobilities, and a time-dependent current of incident ions is measured at the detector electrode 15, which constitutes the "ion mobility spectrum."

In the present example, the ion mobility spectrometer 1 further comprises a closed internal gas circuit, in which circulating gas is transported through the measuring tube 10, a membrane inlet 20, a gas pump 30 and a filter 40. Analyte substances are admitted into the internal gas circuit through the membrane inlet 20. The membrane inlet 20 includes two chambers 21, 22, separated from each other by a heated, permeable membrane 23. A sample gas from a sampling location is drawn in at a gas inlet 24 using an external metering pump 25. The sample gas contacts the heated membrane 23, and flows to the gas outlet 26. A portion of the analyte substances in the sample gas permeates through the membrane 23 and is entrained in the circulating gas in the internal gas circuit.

The circulating gas, which may include the analyte substances, flows from the inner membrane chamber 21 to the branching point 61. The circulating gas is split between a side branch 51, directing the flow to the reaction chamber 11 for analysis, and a substance collector 50 for accumulation. The flow resistances in the two branches determine the proportion of the two gas flows at the branching point 61. Analyte substances in the circulating gas are trapped as they pass through the substance collector 50. In some examples, the substance collector 50 is cooled by using a Peltier element 52, which is advantageous when collecting relatively volatile substances. The circulating gas from the side branch 51 passes through the opening 16 into the reaction chamber 11.

The circulating gas is drawn out of the reaction chamber 11 at the grating grid 13 and flows through gas pump 30 and filter 40 towards the branching point 62. The filter 40 cleans the circulating gas from analyte substances and moisture. The humidity of the circulating gas is maintained by the filter, for example, permanently or for an extended period of time below 100 ppm (parts per million). In another example, the humidity is maintained below 10 ppm. A proportion of the circulating gas that has been cleaned in the filter 40 flows into the drift chamber 12. The cleaned circulating gas flowing from the filter 40 to the drift chamber 12 flows in an opposite direction to the ions in the drift chamber 12. The flow of the cleaned gas into the drift chamber may prevent analyte substances within the reaction chamber 11 from penetrating into the drift chamber 12, which, for example, may prevent falsified analytical results due to reactions between the analyte substances and the existing ions. The remaining portion of the cleaned circulating gas flows back towards the membrane inlet 20, closing the gas circuit. The distribution of the gas flow at the branching point 62 is defined by the flow resistances in the two parallel branches from the branching point 62 to the two gas connections 16 and 18 of the measuring tube 10.

During the collecting phase, analyte substances reaching the reaction chamber 11 through the side branch 51 are analyzed in the measuring tube 10, whereas analyte substances reaching the substance collector 50 are collected at the same time. At periodic intervals, the substance collector 50 is shock heated by, for example, inverting the voltages at the Peltier element 52 or using a special heating element. The analyte substances released by the heat enter the reaction chamber 11 in short substance pulses with enriched concentration. The stored analyte substances are simultaneously desorbed and injected into the measuring tube 10. The collection and the pulsed release make it possible to measure analyte substances whose concentration lie considerably below the detection limit observed during the collecting phase.

Switching valves or other flow elements with electronically adjustable flow resistance may be placed in the side branch 51 or in the branch having the substance collector 50, such that the proportions of the gas flow through the two parallel branches may be changed where appropriate.

In one example, the substance collector 50 includes a capillary tube with, for example, Tenax granules. In another example, the substance collector 50 includes a surface covered with capture molecules whose affinity for one analyte substance or group of analyte substances, for example explosives or drugs, is greater than for other analyte substances or groups of analyte substances. In another example, it is advantageous where the collecting element 50 includes a short piece of GC capillary with metallic substrate material, which may be directly heated by electrical currents. Due to the low thermal mass of the GC capillary, very short substance pulses with high concentrations may be obtained. Where a relatively short capillary tube or a substance collector with a small area of surface-active coating is used, the collection may be incomplete. A portion of the analyte substance passes through the substance collector and into the reaction chamber 11. In this example, the side branch 51 may be omitted.

Figure 2A:
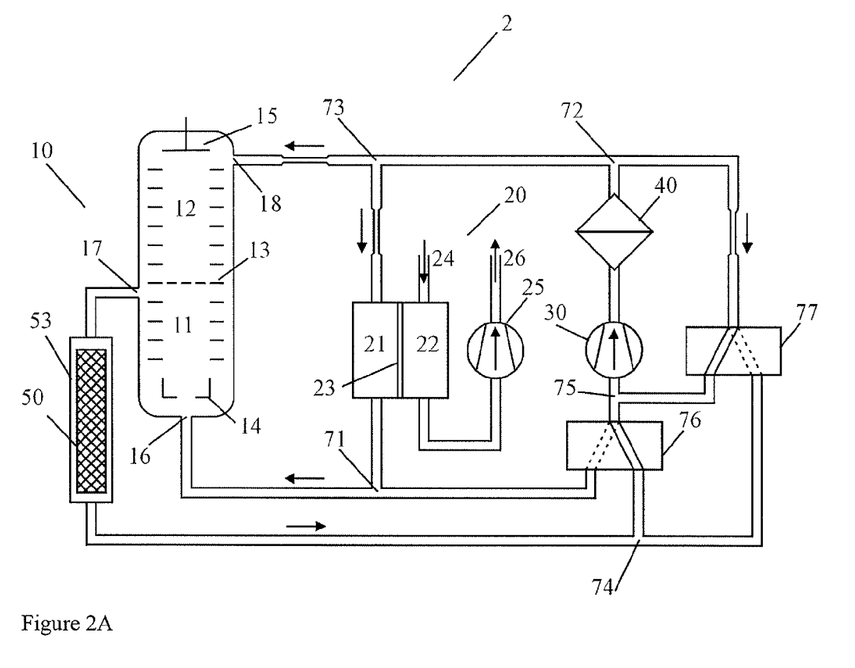
FIGS. 2A to 2C illustrate a second example of the ion mobility spectrometer in a collection phase, a desorption phase and an injection phase, respectively.
Figure 2B:
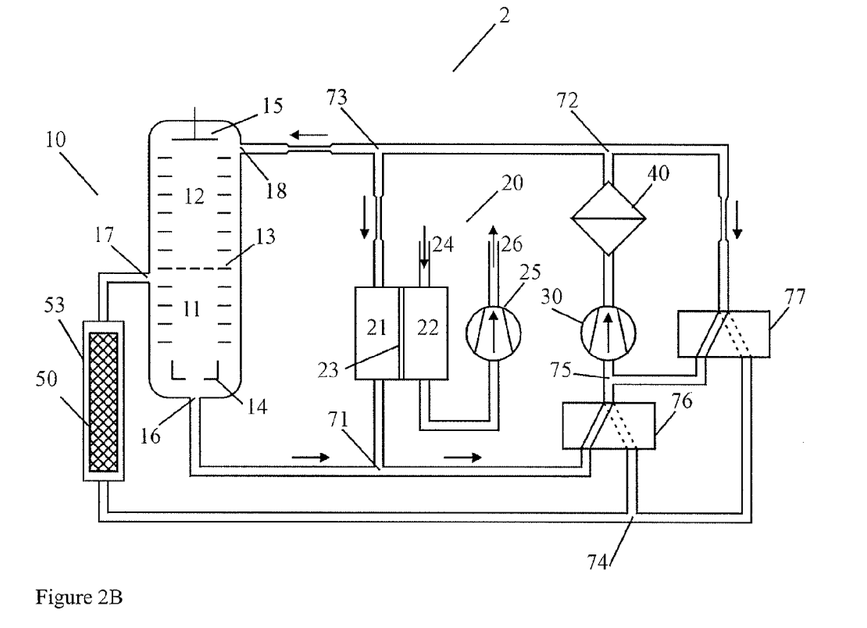
Figure 2C:
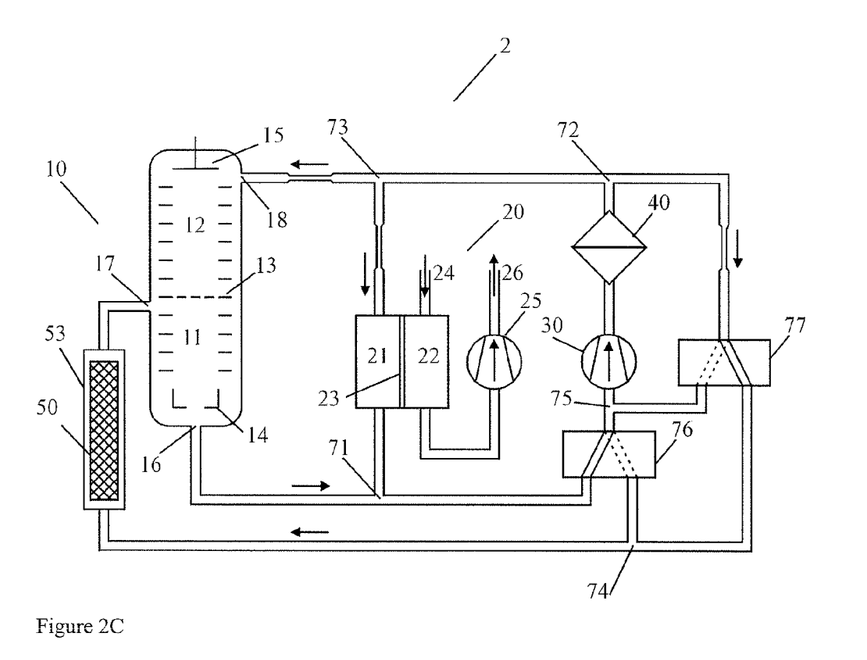

FIGS. 2A to 2C illustrate a second example of an ion mobility spectrometer 2 having the internal substance collector 50. The ion mobility mass spectrometer 2 comprises a measuring tube 10, for example a drift time measuring tube, and a gas circuit. The gas circuit comprises a membrane inlet 20, through which substances are brought into the internal gas circuit, a gas pump 30, a filter 40 for cleaning and dehumidifying the circulating gas and two 3/2-way valves 76 and 77. The design and the electrical function of the measuring tube 10 correspond to those in the foregoing example.

"3/2-way valve" (i.e., 3 connections, 2 positions) designates a valve that switches a gas flow from a central connection into two alternative directions, or end connections.

In all switching states of both the 3/2-way valves 76, 77, a proportion of the cleaned circulating gas is fed through the gas connection 18 into the drift chamber 12. A second partial gas stream flows through the chamber 21 on the internal circuit side of the membrane inlet 20. The other chamber 22 of the membrane inlet 20 is connected to a metering pump 25 that, for example, continually draws sample gas from the gas inlet 24 along a heated membrane 23 and blows the gas to the gas outlet 26. The function of the other branches of the gas circuit depends on the way the two 3/2-way valves 76, 77 are switched.

FIG. 2A illustrates the ion mobility spectrometer 2 in a collecting phase. The gas flows through the chamber 21, on the internal gas circuit side of the membrane inlet 20, into the reaction chamber 11 through the branching point 71. The gas flow is drawn out of the reaction chamber 11 at the gas connection 17 together with the circulating gas that has been fed into the drift chamber 12. A proportion of the analyte substances introduced into the reaction chamber 11 is ionized creating analyte ions. The analyte ions generate a corresponding ion current signal in response to the pulsed opening of the gating grid 13 and the corresponding measured ion mobility spectra are evaluated for continuous monitoring with a moderate sensitivity. The $^{63}$Ni source, of the usual size and activity, ionizes a relatively small proportion of the analyte substances. Therefore, the circulating gas drawn from the reaction chamber 11 still includes almost the full quantity of analyte substances that penetrated from the sample gas through the membrane 23 and into the internal gas circuit. This gas flow is fed through the substance collector 50 and the 3/2-way valve 76 back to the gas pump 30. In some examples, this gas flow path causes a large proportion of the analyte substances contained in the gas flow to be adsorbed in the substance collector 50, where the remaining analyte substances are trapped in the filter 40. As a result, the collection of analyte substances and the investigation of fresh sample gas take place simultaneously and may not require any additional gas pumps.

Another flow of gas in the internal gas circuit passes from the filter 40 through the branching point 72 and the 3/2-way valve 77 directly back to the gas pump 30. The flow resistance in this branch of the gas circuit may be selected such that more gas flows in the two other branches to the measuring tube 10.

FIG. 2B illustrates the ion mobility spectrometer 2 in a desorption phase. In comparison with FIG. 2A, the 3/2-way valve 76 is configured such that circulating gas is drawn through the gas connection 16 out of the reaction chamber 11 and out of the chamber 21. The internally circulating gas containing analyte substances which emerges from the membrane inlet 20 is fed directly to the filter 40, isolating the measuring tube 10 from the membrane inlet 20. Gas continues to flow through both the chambers 21, 22 of the membrane inlet 20, such that the supply of analyte substances from the sample gas into the internal gas circuit is not interrupted.

The substance collector 50 is separated on one side from the internal gas circuit by the two 3/2-way valves 76, 77 such that no gas flows through it. However, the substance collector 50 remains connected to the measuring tube 10 via the gas connection 17. The substance collector 50 is rapidly heated by a heating element 53, relatively quickly releasing the trapped analyte substances. In the present example, the rapid heating occurs simultaneously with a switchover to the desorption phase. In the desorption phase, circulating gas does not flow through the substance collector 50 and, for example, only a relatively small proportion of the released analyte substances reach the reaction chamber 11 by diffusion or as a result of thermal expansion.

FIG. 2C illustrates an injection phase of the ion mobility spectrometer 2. In comparison with FIG. 2B, the substance collector 50 is connected through the 3/2-way valve 77 to the gas circuit at both ends. Cleaned circulating gas flows from the branching point 72 through the substance collector 50 and into the reaction chamber 11. In comparison with the collecting phase, the circulating gas flows through the substance collector 50 in the opposite direction. The released analyte substances enter the reaction chamber 11 at the gas connection 17. The release analyte substances are partially ionized as they flow through the reaction chamber 11, resulting in a corresponding signal in the ion mobility spectrum. The ion mobility spectra are evaluated by periodic flash monitoring, for example having the highest sensitivity, to detect possibly dangerous analyte substances of, for example, the lowest concentration.

The desorption period for the analyte substances is considerably shorter than the collection period. Therefore, the quantity of gas flowing through the substance collector 50 during the injection period is correspondingly smaller. The concentration of analyte substances in the reaction chamber 11 during the injection phase is considerably higher. Therefore, analyte substances may be detected which are below the detection limit observed during the continuous monitoring of the collection phase.

By heating the substance collector 50 relatively slowly in accordance with a specified time function during the injection phase, it is possible to operate the ion mobility spectrometer 2 in a manner comparable to thermal desorption spectrometry (TDS). The enriched substances in the present example are released with desorption rates that are inversely proportional to their adsorption energies to yield a rough temporal separation between highly volatile analyte substances, which are desorbed at low temperatures, and analyte substances of low volatility. In order to obtain supplementary information through TDS, time series of ion mobility spectra are recorded with specific delays after switching into the injection phase or synchronously with the temperature change at the substance collector 50. As a result, the different analyte substances in the measured ion mobility spectra become visible after characteristic times or at characteristic temperatures. Coupling the TDS and IMS yields a two-dimensional signal in which the desorption temperature of the analyte substances and the drift time in the drift chamber 12 represent independent parameter axes. The time series of the ion mobility spectra may be thought of as a series of thermal desorption spectra for each of the ion types distinguishable in the ion mobility spectrum. Separation with respect to two independent parameters allows more definite identification to be achieved than is possible with a plain ion mobility spectrometer. In some examples, it is only possible to distinguish two different substances when they are separated by desorption temperature. This happens when both analyte substances exhibit the same drift time and therefore normally overlap in the ion mobility spectrum.

FIGS. 3A to 3D illustrate a third example of an ion mobility spectrometer 3 having the internal substance collector 50 and an additional internal gas chromatographic column 90 for separation of the analyte substances. The ion mobility spectrometer 3 further comprises a measuring tube 10 and an internal gas circuit. The internal gas circuit includes a membrane inlet 20, a gas pump 30, a filter 40, a 3/2-way valve 87 and two 2/2-way valves 88, 89. The control valves 87, 88, 89 determine four operating states of the ion mobility spectrometer 3: a collection phase, a purging phase, a desorption phase and an injection/chromatography phase. Design and electrical function of the measuring tube 10 correspond to those in the foregoing examples.

In the switching states of the control valves 87, 88, 89, a proportion of the cleaned circulating gas is fed through the gas connection 18 into the drift chamber 12 of the measuring tube 10. A second partial gas stream flows through the chamber 21 on the internal circuit side of the membrane inlet 20. The function of the other branches depends on the particular switching states of the control valves 87, 88, 89.

Figure 3A:
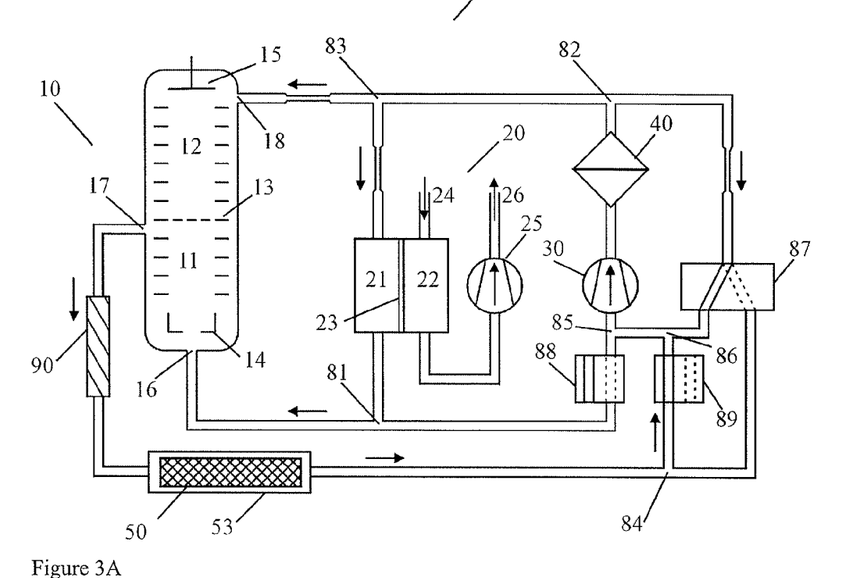
FIGS. 3A to 3D illustrate a third example of the ion mobility spectrometer in a collection phase, a purging phase, a desorption phase, and an injection/chromatography phase, respectively.

FIG. 3A illustrates the ion mobility spectrometer 3 in the collecting phase. Cleaned circulating gas reaches the inner chamber 21 of the membrane inlet 20 through the branching point 83. The circulating gas, for example which contains analyte substances, is fed through the branching point 81 into the reaction chamber 11 of the measuring tube 10. The gas flows through the chamber 11 and is drawn out at gas connection 17, together with the circulating gas that has been introduced into the drift chamber 12. The circulating gas that still has almost the full quantity of analyte substances is fed through the gas chromatographic separation column 90 and through the substance collector 50. In the collection phase, the separation column 90 is heated to a sufficient level for the substances to pass through it with relatively no delay. As a result, the majority of analyte substances contained in the gas flow are adsorbed when they reach the substance collector 50. The remaining analyte substances pass from the substance collector 50 through the 2/2-way valve 89 and the gas pump 30 to the filter 40, where they are, for example, completely trapped. Analyte substance collection and normal monitoring analysis simultaneously occur and additional gas pumps may not be needed. A short, packed column or a multi-capillary column with a low flow resistance is used as the gas chromatographic separation column 90.

Figure 3B:
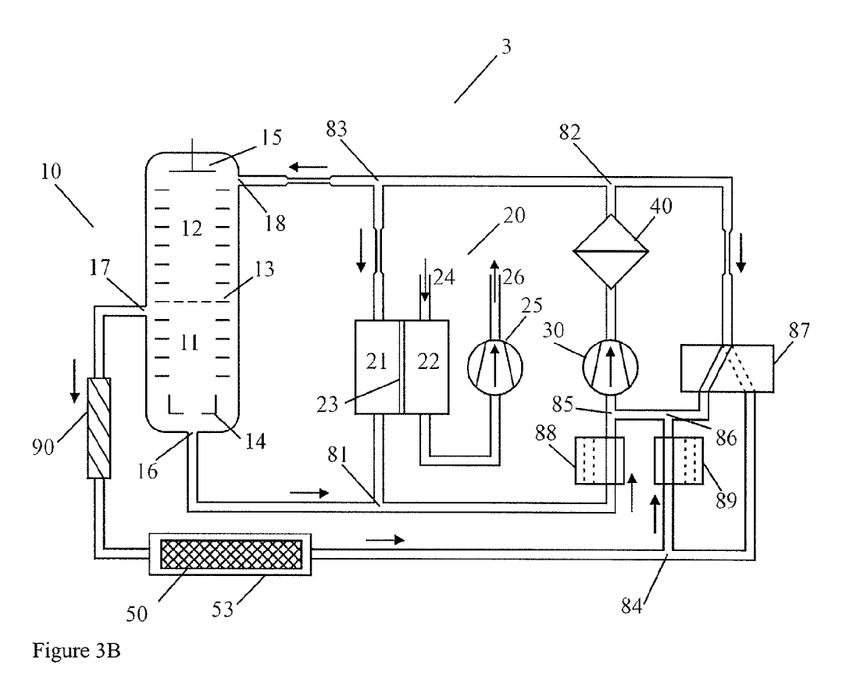

FIG. 3B illustrates the ion mobility spectrometer 3 in the phase where the separation column 90 is purged. In comparison with FIG. 3A, the 2/2-way valve 88 is configured to draw the circulating gas out of the reaction chamber 11 and out of the inner chamber 21. The circulating gas containing analyte substances is fed directly to the filter 40 by the gas pump 30, isolating the measuring tube 10 from the membrane inlet 20. However, gas continues to flow through both chambers 21, 22 of the membrane inlet 20, such that the supply of analyte substances from the sample gas into the gas circuit is uninterrupted and the balanced conditions for the supply of analyte substances through the membrane remain untouched.

In the present example, relatively little or no analyte substances flow through the measuring tube 10 or the separation column 90 connected to it, due to the isolation from the membrane inlet 20. The few low volatility analyte substances which were retained by the separation column are released from the heated separation column 90 and carried by the flow of gas into the substance collector 50, where they are trapped. The purging phase may be maintained for the entire occurring or expected retention time. When the purging is complete, the temperature of the separation column 90 is reduced to a level suitable for the subsequent separation of substances, or to the starting temperature of a temperature program being used.

Figure 3C:
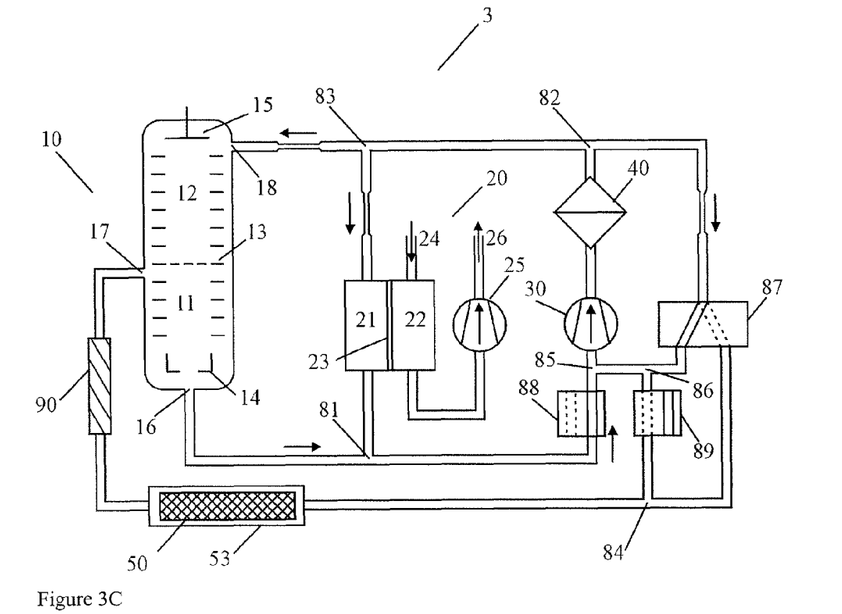

FIG. 3C illustrates the ion mobility spectrometer 3 in the desorption phase. The 2/2-way valve 88 remains configured to connect the gas pump 30 through the branching point 81. As a result, the circulating gas is drawn out of the reaction chamber 11 through the gas connection 16, and out of the inner membrane chamber 21. The gas in the measuring tube 10 remains isolated from the membrane inlet 20. The substance collector 50 and the separation column 90 are also separated from the gas circuit on one side by the 2/2-way valve 89. The substance collector 50 is heated, simultaneously with the switchover to the desorption phase, such that the previously stored analyte substances are released in the shortest possible time into a relatively small volume of resting gas. As circulating gas does not flow through the substance collector 50 in the desorption phase, only a relatively small proportion of the released analyte substances reach the separation column 90 as a result of diffusion or as a consequence of thermal expansion of the resting gas.

Figure 3D:
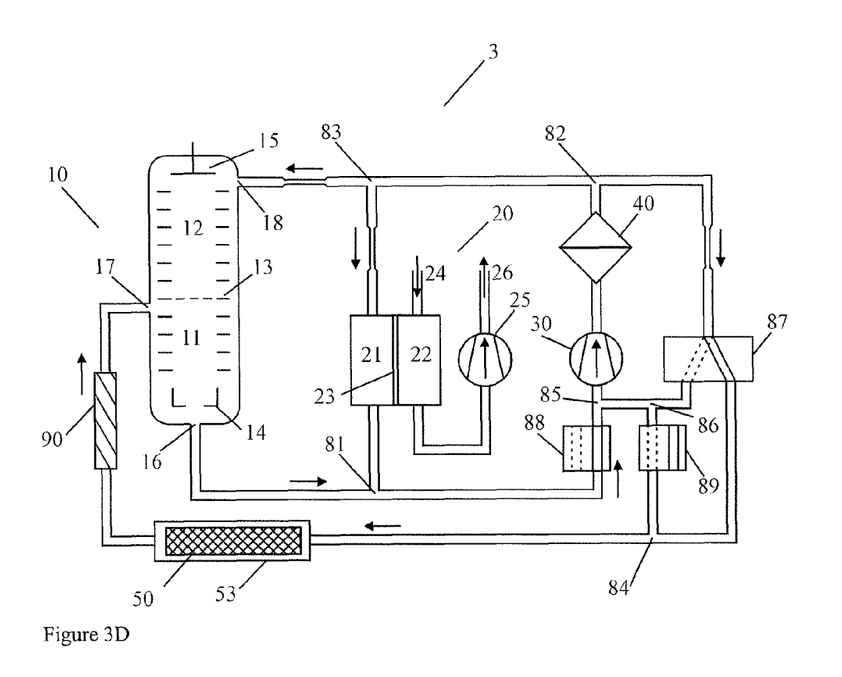

FIG. 3D illustrates the ion mobility spectrometer 3 in the injection/chromatography phase. The ion mobility spectrometer 3 is switched to the injection/chromatography phase after heating the substance collector 50 to the desorption temperature. The two 2/2-way valves 88, 89 remain in the same configuration as in the desorption phase. However, the substance collector 50 and the separation column 90 are connected with the gas circuit at both ends by the 3/2-way valve 87, such that cleaned circulating gas flows through the substance collector 50 and the separation column 90 into the reaction chamber 11.

The analyte substances released in the substance collector 50 flow through the separation column 90, where different analyte substances are separated in time by the different retention times of the substances, and enter the reaction chamber 11. Time series of ion mobility spectra are recorded synchronously with the switchover to the desorption phase. The different analyte substances may become visible, for example, only in the ion mobility spectra acquired at the correct substance-characteristic retention times. Coupling together gas chromatography (GC) and ion mobility spectrometry yields a two-dimensional signal in which the retention time in the separation column 90 and the drift time in the drift chamber 12 represent independent axes (parameters). The result may be either a time series of ion mobility spectra measured at certain times or a series of chromatograms for each of the different ion types found in the ion mobility spectrum. Separation with respect to two independent parameters, for example drift time and retention time, permits more definite identifications to be achieved than is possible with a plain ion mobility spectrometer. The separation of substances in a GC capillary is, generally, significantly better than with thermal desorption analysis. As a result, the mutual overlap between different analyte substances in the ion mobility spectrum may be further reduced. In contrast to a combination of a substance collector and a prior art gas chromatograph outside the gas circuit, the ion mobility spectrometer 3 offers all the advantages of a closed gas circuit with a membrane inlet. A simple and relatively compact GC/IMS coupling is achieved with no additional transport or gas supply devices. In the GC/IMS arrangement, the switching valves are not located upstream of the measuring tube 10 in the gas path of the desorbed analyte substances or substances separated by gas chromatography. Therefore, inexpensive standard valves may be used in place of inert or heated GC valves.

Figure 4A:
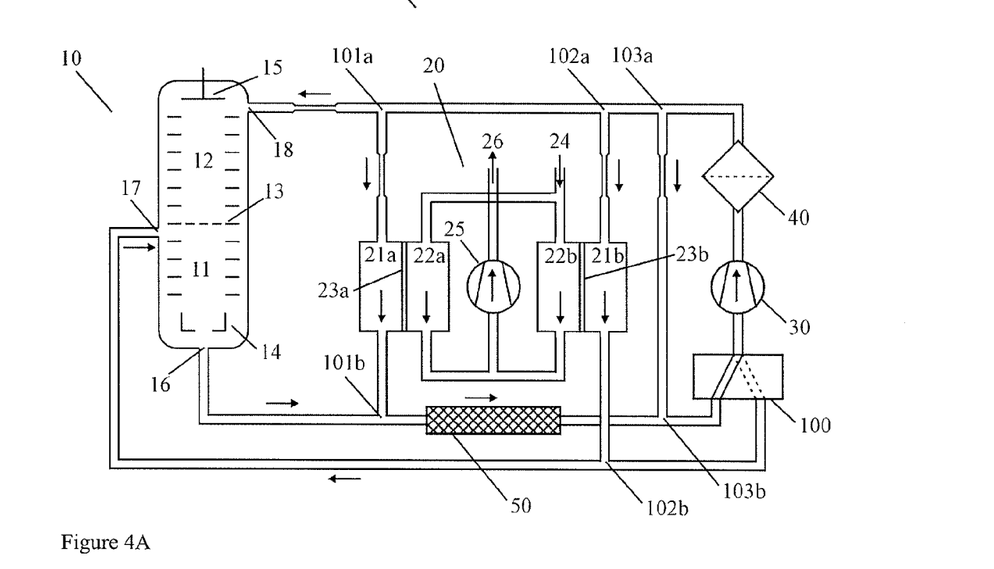
FIGS. 4A and 4B illustrate a forth example of the ion mobility spectrometer having a double membrane inlet.
Figure 4B:
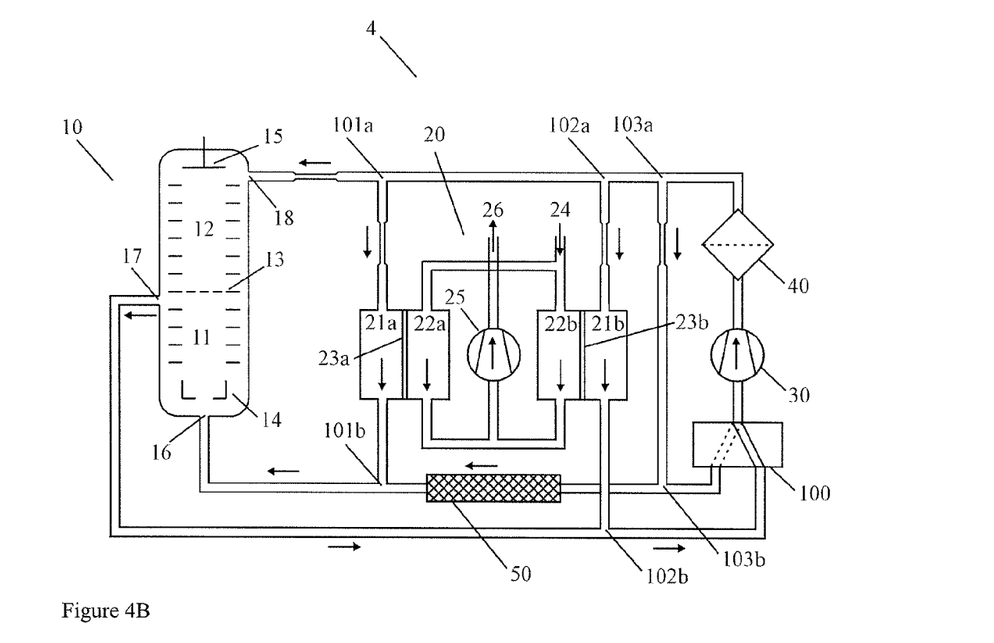

FIGS. 4A and 4B illustrate a fourth example of an ion mobility spectrometer 4 comprising the internal substance collector 50 and a double membrane inlet with two membranes 23a, 23b sampling both analyte substances from the same sampling location. In the present example, the supply of analyte substances to the substance collector may be doubled while maintaining the normal sensitivity of the monitoring mode.

The circulating gas cleaned in the filter 40 is divided at the three branching points 101a, 102a, 103a, and flows into the drift chamber 12, to one of the two parallel chambers 21a, 21b and into a side branch that runs from the branching point 103a to the branching point 103b. The membrane inlet 20 supplies the analyte substances, where the membrane inlet 20 comprises two internal chambers 21a, 21b and two external chambers 22a, 22b. The two internal chambers 21a, 21b and the two external chambers 22a, 22b are separated from each other by heated permeable membranes 23a, 23b. The sample gas is drawn in from the sampling location at the gas inlet 24, for example using an external metering pump 25, and flows along the two heated membranes 23a, 23b to the gas outlet 26. In this way, the same sample gas is continuously exposed to the two membranes 23a, 23b. A portion of the analyte substances in the sample gas passes through the membranes 23a, 23b and enters the internal gas circuit.

FIG. 4A illustrates the collection phase, collecting analyte substances from both inner membrane chambers 21a and 21b and monitoring the analyte substances from membrane chamber 21b. The 3/2-way valve 100 is configured to feed circulating gas, for example containing analyte substances, from chamber 21b through a branching point 102b into the reaction chamber 11 for analysis. The two branching points 101b and 103b are connected to the suction side of a gas pump 30 through the 3/2-way valve 100. At the gas connection 16, circulating gas is drawn out of the reaction chamber 11 and flows, together with the circulating gas that contains analyte substances from the chamber 21a, to the gas pump 30. Accordingly, both partial gas streams flow through the substance collector 50 located between the branching points 101b and 103b. Cleaned circulating gas flows through the branching point 103b from the side branch back to the gas pump 30.

In the collection phase, only substances from the chamber 21b enter the reaction chamber 11. However, the majority of the analyte substances are not ionized in the reaction chamber 11, but pass to the substance collector 50 together with the drawn out circulating gas and the substances from the chamber 21a. In the substance collector 50, the analyte substances to be detected are accumulated. Collection of substances in the substance collector 50 occurs simultaneously with direct monitoring of the sample gas.

FIG. 4B illustrates the desorption/injection phase. The 3/2-way valve 100 is switched into a second state, where the branching point 102b is connected to the suction side of the gas pump 30. In the second state, circulating gas is drawn out of the reaction chamber 11 through the gas connection 17 and fed to the gas pump 30 together with the circulating gas that contains substances from the membrane chamber 21b. However, circulating gas containing analyte substances flows from the membrane chamber 21a and enters the reaction chamber 11 through the gas connection 16. When the 3/2-way valve 100 is switched into this state, the chamber 21a is switched into a monitoring mode, while the chamber 21b is isolated.

Cleaned circulating gas also flows from the side branch to the substance collector 50. Where the substance collector 50 is heated to an appropriate desorption temperature synchronously with the switching of the 3/2-way valve 100, the analyte substances that have accumulated in the substance collector 50 are released in a short desorption pulse. The released analyte substances enter the reaction chamber 11 together with the analyte substances from the chamber 21a through the gas connection 16. The analyte substances from the substance collector 50 and the chamber 21a are analyzed, for example simultaneously, in the measuring tube 10. Where, for example, the substance concentrations in the sample gas have not changed compared to the period of enrichment, a short increase in concentration of analyte substances enter the reaction chamber 11, yielding a corresponding measurement signal. The enrichment permits the detection of analyte substances of low volatility, whose concentrations lie above the detection power when the two chambers 21a, 21b are in metering mode.

The ion mobility spectrometer 4, for example, allows for the continuous monitoring of the sample gas and, in parallel, to collect substances of low volatility cyclically over specific periods of time. The low volatility substances may be analyzed by a short desorption pulse in the measuring tube 10. Advantageously, during the collecting phase, the analyte substances from both chambers 21a, 21b are accumulated in the substance collector 50. In addition, in both of the switched states, the two chambers 21a, 21b are, for example, continuously flushed with cleaned circulating gas, such that a saturation of the membranes 23a, 23b and of the circulating gas in the chambers 21a, 21b may be prevented.

Those skilled in the art may be able to develop further embodiments according to this disclosure. Particularly, ion mobility spectrometers according to the disclosure are not restricted to the drift time type, but can favorably be employed with any ion mobility spectrometer that has a closed internal gas circuit.

Although the present invention has been illustrated and described with respect to several preferred embodiments thereof, various changes, omissions and additions to the form and detail thereof, may be made therein, without departing from the spirit and scope of the invention.

What is claimed is:

1. An ion mobility spectrometer, comprising:
a substance collector;
a measuring tube coupled to the substance collector, the measuring tube having a reaction chamber and a drift chamber;
a membrane inlet coupled to at least one of the substance collector and the measuring tube, the membrane inlet having an inner chamber; and
a filter coupled to a pump in a closed internal gas circuit, the closed internal gas circuit defined by the substance collector, the measuring tube and the membrane inlet.

2. The ion mobility spectrometer of claim 1, wherein the substance collector is configured in a circulating gas flow path between the inner chamber and the reaction chamber.

3. The ion mobility spectrometer of claim 1, wherein
the substance collector is coupled to the measuring tube through the reaction chamber; and
the internal gas circuit is further defined by a plurality of control elements, the control elements having a first switching state and a second switching state, the first switching state coupling the reaction chamber and the substance collector through an analyte substance containing gas flow path, the second switching state coupling the filter, the substance collector and the reaction chamber through a cleaned circulating gas flow path.

4. The ion mobility spectrometer of claim 3, wherein each control element comprises at least one of a valve and a controllable flow resistance.

5. The ion mobility spectrometer of claim 3, wherein the control elements are not coupled between the substance collector and the reaction chamber.

6. Ion mobility spectrometer of claim 3, wherein
the control elements are not coupled in a circulating gas flow path between the inner chamber and the substance collector; and
the control elements are not coupled in a second circulating gas flow path between the inner chamber and the reaction chamber.

7. The ion mobility spectrometer of claim 1, wherein
the reaction chamber further comprises a first gas connection and a second gas connection;
the drift chamber further comprises a third gas connection;
the inner chamber is coupled to the first gas connection and a first end connection of a first 3/2-way valve;
the second gas connection is coupled to a second end connection of the first 3/2-way valve through a branching point;
the substance collector is configured between the second gas connection and the branching point; and
the pump further comprises a pressure side and a suction side, the pressure side of the pump is coupled to, through at least one of a direct path and a path through the filter, the third gas connection, the inner chamber and a center connection of a second 3/2-way valve, the suction side of the pump is coupled to a center connection of the first 3/2-way valve and a second end of the second 3/2-way valve.

8. The ion mobility spectrometer of claim 1, wherein
the memory inlet further comprising a second inner chamber, the inner chamber and the second inner chamber are configured in parallel;
the measuring tube further comprises first, second and third gas connections;
the pump further comprises a pressure side and a suction side, the pressure side is coupled to, through at least one of a direct path and a path through the filter, the first gas connection, the inner chambers and, through a side branch, a first end connection of a 3/2-way valve, the suction side is coupled to a center connection of the 3/2-way valve;
the inner chamber is coupled through a first branching point to the second gas connection and the first end connection of the 3/2-way valve;
the second inner chamber is coupled through a second branching point to the third gas connection and a second end connection of the 3/2-way valve; and
the substance collector is configured between the first branching point and a connection of a side branch of the first end connection of the 3/2-way valve.

9. The ion mobility spectrometer of claim 1, wherein the substance collector is thermally joined to a heating element.

10. The ion mobility spectrometer of claim 1, wherein the substance collector is thermally joined to a cooling element.

11. The ion mobility spectrometer of claim 1, wherein the substance collector further comprises at least one surface having capture molecules, the capture molecules operable to have an affinity greater for a first analyte substance than for at least one of other analyte substances and groups of analyte substances.

12. The ion mobility spectrometer of claim 1, wherein the substance collector comprises a capillary tube having Tenax granules.

13. The ion mobility spectrometer of claim 1, further comprising a gas chromatographic separating column coupled between the substance collector and the measuring tube in the closed internal gas circuit.

14. The ion mobility spectrometer of claim 13, wherein the gas chromatographic separating column further comprises a heating element.

15. A method, comprising:
- providing an ion mobility spectrometer comprising a measuring tube, a substance collector and a membrane inlet, the measuring tube, the substance collector and the membrane inlet defining a closed internal gas circuit;
- separating the closed internal gas circuit from an external sample gas flow through the membrane inlet;
- transferring circulating gas containing an analyte substance from the membrane inlet to the substance collector, the analyte substance accumulated in the substance collector;
- releasing the accumulated analyte substances; and
- transferring the released analyte substances to the measuring tube.

16. The method of claim 15, further comprising at least one of
- cooling the substance collector during collection; and
- heating the substance collector during collection.

17. The method of claim 15, further comprising at least one of
- heating the substance collector periodically in accordance with a time function for a thermal desorption analysis; and
- heating the substance collector continuously in accordance with the time function for the thermal desorption analysis.

18. The method of claim 15, wherein the circulating gas containing the analyte substance from the membrane inlet to the substance collector is transferred through the measuring tube.

19. The method of claim 18, wherein the direction of gas flow through the substance collector is reversed between the transferring of the circulating gas and the transferring of the released analyte substances.

* * * * *